US012599374B2

(12) United States Patent (10) Patent No.: US 12,599,374 B2
Xu et al. (45) Date of Patent: Apr. 14, 2026

(54) DOUBLE-BENDING FLEXIBLE SURGICAL TOOL SYSTEM

(71) Applicant: BEIJING SURGERII ROBOTICS COMPANY LIMITED, Beijing (CN)

(72) Inventors: Kai Xu, Beijing (CN); Jiangran Zhao, Beijing (CN); Linhui Niu, Beijing (CN); Yi Sun, Beijing (CN); Jing Zhu, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 1326 days.

(21) Appl. No.: 17/418,881

(22) PCT Filed: Dec. 27, 2019

(86) PCT No.: PCT/CN2019/129312
§ 371 (c)(1),
(2) Date: Jun. 28, 2021

(87) PCT Pub. No.: WO2020/135753
PCT Pub. Date: Jul. 2, 2020

(65) Prior Publication Data
US 2022/0071611 A1 Mar. 10, 2022

(30) Foreign Application Priority Data

Dec. 28, 2018 (CN) .......................... 201811619535.1
Jun. 5, 2019 (CN) .......................... 201910486486.7

(51) Int. Cl.
*A61B 17/00* (2006.01)
*A61M 25/01* (2006.01)
(52) U.S. Cl.
CPC ................... *A61B 17/00234* (2013.01); *A61B 2017/00314* (2013.01); *A61B 2017/00318* (2013.01); *A61M 25/0144* (2013.01)

(58) Field of Classification Search
CPC ......... A61B 34/70; A61B 34/71; A61B 34/30; A61B 2034/715; A61B 2034/301;
(Continued)

(56) References Cited

U.S. PATENT DOCUMENTS

2005/0096694 A1* 5/2005 Lee ................ A61B 17/320016
606/205
2006/0079889 A1 4/2006 Scott
(Continued)

FOREIGN PATENT DOCUMENTS

CA 2103319 A1 5/1994
CN 103085083 A 5/2013
(Continued)

OTHER PUBLICATIONS

Office Action in related Canadian Application No. 3,118,940, dated Aug. 23, 2022 (7 pages).
(Continued)

*Primary Examiner* — Diane D Yabut
(74) *Attorney, Agent, or Firm* — Bayes PLLC

(57) ABSTRACT

A double-bending flexible surgical tool system includes a mechanical arm including a first continuum segment, a rigid connection segment, a second continuum segment, and a third continuum segment. The first continuum segment and the second continuum segment are associated to form a first dual continuum mechanism. A proximal continuum segment disposed at a proximal end of the first continuum segment and associated with the third continuum segment disposed at a distal end of the second continuum segment form a second dual continuum mechanism. A transmission driving unit associated with the rigid connection segment and the proximal continuum segment, respectively, is configured to drive the first continuum segment to bend in any direction to drive the second continuum segment to bend in an opposite (Continued)

direction, and to drive the proximal continuum segment to bend in any direction to drive the third continuum segment to bend in an opposite direction.

13 Claims, 8 Drawing Sheets

(58) Field of Classification Search
CPC ...... A61B 17/00234; A61B 17/320016; A61B 2017/00318; A61B 2017/00323; A61B 2017/00327; A61B 2017/2904; A61B 2017/2908; A61B 2017/2919; A61B 1/0057; A61M 25/0144; A61M 25/0147; B25J 9/065; B25J 9/104; B25J 9/1045; B25J 9/1625
See application file for complete search history.

(56) References Cited

U.S. PATENT DOCUMENTS

| | | | |
|---|---|---|---|
| 2012/0253131 A1* | 10/2012 | Malkowski | ............ A61B 34/30 |
| | | | 606/1 |
| 2017/0172678 A1 | 6/2017 | Dewaele et al. | |

FOREIGN PATENT DOCUMENTS

| | | | |
|---|---|---|---|
| CN | 103654694 | A | 3/2014 |
| CN | 106361387 | A | 2/2017 |
| CN | 108245254 | A | 7/2018 |
| CN | 109498154 | A | 3/2019 |
| CN | 110037795 | A | 7/2019 |
| JP | 2007503285 | A | 2/2007 |
| JP | 2015147059 | A | 8/2015 |
| KR | 20160124795 | A | 10/2016 |
| WO | 2018041159 | A1 | 3/2018 |
| WO | 2018041204 | A1 | 3/2018 |

OTHER PUBLICATIONS

Office Action in related Korean Application No. 10-2021-7023739 dated Jan. 19, 2023 (9 pages).

Zhao et al., "Continuum Manipulator with Redundant Backbones and Constrained Bending Curvature for Continuously Variable Stiffness", 2018 IEEE/RSJ International Conference on Intelligent Robots and Systems (IROS), Oct. 1-5, 2018, pp. 7492-7499 (8 pages).

Chinese Office Action in corresponding Chinese Application No. 2019104864867 dated Dec. 24, 2019 (3 pages).

International Search Report in corresponding PCT Application No. PCT/CN2019/129312 dated Mar. 27, 2020 (6 pages).

Office Action in related Japanese Application No. 2021-533729, dated Jun. 7, 2022 (9 pages).

Supplementary European Search Report in corresponding European Application No. EP19904087 dated Jan. 11, 2022 (3 pages).

* cited by examiner

DOUBLE-BENDING FLEXIBLE SURGICAL TOOL SYSTEM

CROSS-REFERENCE TO RELATED APPLICATIONS

This patent application is a U.S. National Phase of International Application No. PCT/CN2019/129312, filed on Dec. 27, 2019, which claims priority to Chinese Patent Application No. 201811619535.1, filed on Dec. 28, 2018, and Chinese Patent Application No. 201910486486.7, filed on Jun. 5, 2019. The entire contents of each of the above-identified applications are incorporated herein by reference.

TECHNICAL FIELD

The disclosure relates to a medical instrument, in particular to a double-bending flexible surgical tool system based on a dual continuum mechanism.

BACKGROUND

Multi-port laparoscopic minimally invasive surgery plays an important role in surgical operations due to small wound and fast postoperative recovery. The conventional da Vinci surgical robot of Intuitive Surgical Inc. assists surgeons in completing the multi-port laparoscopic minimally invasive surgery, and gets great commercial success.

After the multi-port laparoscopic surgery, single-port laparoscopic surgery and non-invasive surgery through natural orifice are developed. They have smaller wound and faster postoperative recovery. But in single-port laparoscopic surgery and non-invasive surgery through the natural orifice, all surgical instruments including visual illumination module and surgical operating arm reach a surgical site through a single channel, which has strict requirements on preparation of surgical instruments. Distal structures of the present surgical instruments are mainly multiple rods hinged in serial and driven by pulling force of steal wires, so that distal instruments can bend at the hinges. Because the steel wire rope needs to be kept in a continuous tensioning state through pulleys, due to this driving manner, further miniaturization of the surgical instrument is difficult to achieve and movement performance of the surgical instrument is difficult to further improve.

Flexibility of existing surgical instruments is limited by the driving manner of the rigid structure and the wire rope, and its volume is relatively large. Although the Intuitive Surgical Inc. recently launched da Vinci Single-site (SS-type da Vinci) surgical robot, the original rigid surgical instrument is changed into a semi-rigid surgical instrument, and a pre-bending sleeve is introduced, which, to a certain extent, improves the movement performance of the surgical instruments, but still cannot fundamentally solve the problems faced by the traditional surgical instruments.

SUMMARY

In view of the above problems, an objective of the present disclosure is to provide a double-bending flexible surgical tool system based on a dual continuum mechanism. The flexible surgical tool system can be applied to a natural orifice or a single surgical incision of a human body and perform operations.

To this end, present disclosure provides a double-bending flexible surgical tool system comprising: a mechanical arm comprising a first continuum segment, a rigid connection segment, a second continuum segment and a third continuum segment, the first continuum segment and the second continuum segment being associated to form a first dual continuum mechanism; a proximal continuum segment disposed at a proximal end of the first continuum segment and associated with the third continuum segment disposed at a distal end of the second continuum segment to form a second dual continuum mechanism; a transmission driving unit associated with the rigid connection segment and the proximal continuum segment, respectively, and operable to drive the first continuum segment to bend in any direction to drive the second continuum segment to bend in an opposite direction, and to drive the proximal continuum segment to bend in any direction to drive the third continuum segment to bend in an opposite direction.

A double-bending flexible surgical tool system comprises: a mechanical arm comprising a first continuum segment, a rigid connection segment, a second continuum segment and a third continuum segment, the first continuum segment and the second continuum segment being associated to form a first dual continuum mechanism, and the third continuum segment being disposed at a distal end of the second continuum segment; a transmission driving unit associated with the rigid connection segment and the third continuum segment, respectively, and operable to drive the first continuum segment to bend in any direction to drive the second continuum segment to bend in an opposite direction, and to directly drive the third continuum segment to bend in any direction.

In the double-bending flexible surgical tool system, the transmission driving unit comprises a plurality of linear motion mechanisms consisting essentially of a double-threaded rod, a first sliding block, and a second sliding block; the first continuum segment comprises a first continuum fixing disk and direction-controlling continuum structural bones, and the rigid connection segment comprises a rigid connection fixing disk; the direction-controlling continuum structural bones comprises a plurality of pairs, distal ends of each pair of the direction-controlling continuum structural bones are connected with the rigid connection fixing disk, and proximal ends of each pair of the direction-controlling continuum structural bones pass through the first continuum fixing disk and are connected with the first sliding block and the second sliding block, respectively.

In the double-bending flexible surgical tool system, the mechanical arm further comprises a rigid feed segment comprising a plurality of rigid feed segment spacer disks spaced at a proximal side of the first continuum fixing disk; the first continuum segment further comprises a plurality of first continuum spacer disks spaced between a distal side of the first continuum fixing disk and a proximal side of the rigid connection fixing disk; the direction-controlling continuum structural bone sequentially passes through the rigid feed segment spacer disk and the first continuum spacer disk; the second continuum segment comprises a second continuum fixing disk and a plurality of first dual continuum structural bones, a distal end of each first dual continuum structural bone is connected with the second continuum fixing disk, and a proximal end of each first dual continuum structural bone passes through the rigid connection fixing disk and is connected with the first continuum fixing disk.

In the double-bending flexible surgical tool system, the rigid connection segment further comprises a plurality of rigid connection spacer disks spaced at a distal side of the rigid connection fixing disk; the second continuum segment further comprises a plurality of second continuum spacer disks spaced at a proximal side of the second continuum fixing disk; the first dual continuum structural bone sequentially passes through the first continuum spacer disks, rigidly connection spacer disks and second continuum spacer disks.

In the double-bending flexible surgical tool system, the proximal continuum segment comprises a proximal continuum fixing disk and proximal continuum structural bones, the proximal continuum structural bones comprise at least two pairs, distal ends of each pair of the proximal continuum structural bones is connected with the proximal continuum fixing disk, and proximal ends are directly connected with the first sliding block and second sliding block.

In the double-bending flexible surgical tool system, the third continuum segment comprises a third continuum fixing disk and a plurality of second dual continuum structural bones, a distal end of each second dual continuum structural bone is connected with the third continuum distal fixing disk, and a proximal end of each second dual continuum structural bone passes through the first continuum fixing disk, the rigid connection fixing disk and the second continuum fixing disk and is connected with the proximal continuum fixing disk.

In the double-bending flexible surgical tool system, the third continuum segment comprises a third continuum fixing disk and third continuum structural bones, the third continuum structural bones comprises at least two pairs, distal ends of each pair of third continuum structural bones are connected with the third continuum distal fixing disk, and proximal ends of each pair of third continuum structural bones pass through the first continuum fixing disk, the rigid connection fixing disk and the second continuum fixing disk and are connected with the first sliding block and the second sliding block.

The double-bending flexible surgical tool system, further comprises a surgical effector mechanism comprising: a surgical effector disposed on the third continuum fixing disk; a surgical effector control wire, a distal end of the surgical effector control wire being connected with the surgical effector, and a proximal end of the surgical effector control wire passing through the mechanical arm and being connected with the first sliding block or the second sliding block.

In the double-bending flexible surgical tool system, the third continuum segment further comprises a plurality of third continuum spacer disks spaced between a distal side of the third continuum fixing disk and a distal side of the second continuum connection fixing disk, the second dual continuum structural bone and the surgical effector control wire sequentially pass through the rigid feed segment spacer disks, the first continuum spacer disks, the rigid connection spacer disks, the second continuum spacer disks and the third continuum spacer disks.

In the double-bending flexible surgical tool system, the third continuum segment further comprises a plurality of third continuum spacer disks spaced between a distal side of the third continuum fixing disk and a distal side of the second continuum connection fixing disk, the third continuum structural bone and the surgical effector control wire sequentially pass through the rigid feed segment spacer disks, the first continuum spacer disks, the rigid connection spacer disks, the second continuum spacer disks and the third continuum spacer disks.

In the double-bending flexible surgical tool system, the linear motion mechanisms comprises five linear motion mechanisms: a first pair of the linear motion mechanisms each connected with a pair of the direction-controlling continuum structural bones to achieve bending degrees of freedom in two directions for the first continuum segment; a second pair of the linear motion mechanisms each connected with a pair of the proximal continuum structural bones to achieve bending degrees of freedom in two directions for the third continuum segment; and a linear motion mechanism connected with the surgical effector control wire to control an action of the surgical effector.

In the double-bending flexible surgical tool system, the linear motion mechanisms comprises five linear motion mechanisms: a first pair of the linear motion mechanisms each connected with a pair of the direction-controlling continuum structural bones to achieve bending degrees of freedom in two directions for the first continuum segment; a second pair of the linear motion mechanisms each connected with a pair of the third continuum structural bones to achieve bending degrees of freedom in two directions for the third continuum segment; and a linear motion mechanism connected with the surgical effector control wire to control an action of the surgical effector.

The embodiments of present disclosure include the following advantages: 1. in the present disclosure, a first continuum segment, a rigid connection segment, and a second continuum segment are sequentially associated to form a first dual continuum mechanism. A third continuum segment is disposed at distal end of the first dual continuum mechanism. Structural bones of the third continuum segment pass through the first dual continuum mechanism and are connected with the proximal continuum segment to form a second dual continuum mechanism. A transmission driving unit is respectively connected with the rigid connection segment and the proximal continuum segment, or the structural bones of the third continuum segment is directly connected with the transmission driving unit, so that the first dual continuum mechanism and the second dual continuum mechanism/the third continuum segment can be driven by the transmission driving unit to bend in any direction. Thus, the first dual continuum mechanism and the second dual continuum mechanism/third continuum segment form a double-bending mechanical arm. The flexibility of surgical tool movement can be increased and the movement space of the surgical tool can be expanded. A mechanical arm external to human body is able to maintain a fixed position. The surgical tool can have sufficient coverage and achieve accurate control of the surgical action. Thus, the movement performance of the surgical tool is more excellent, and the movement performance of the surgical instrument can be improved, realizing miniaturization and lightening of the surgical instrument. In present disclosure, two ends of the structural bone in the first dual continuum mechanism are respectively fixed at the proximal end of the first continuum segment and the distal end of the second continuum segment. The length of the structural bone remains unchanged during the driving process, so that the total length of the first continuum segment, the rigid connection segment and the second continuum segment remains unchanged. When the transmission driving unit drives the first continuum segment to bend towards a certain direction, the coupling motion of the second continuum segment is also uniquely determined. Similarly, the structural bone of the second dual continuum mechanism or the structural bone of the third continuum segment also remains unchanged in length during driving. When the transmission driving unit drives the proximal continuum segment to bend in a certain direction. The coupling motion of the third continuum segment is also uniquely determined. 3. In present disclosure, the transmission driving unit uses a double-threaded rod and a sliding block as a linear motion mechanism. When the double-threaded rod is driven to rotate, two sliding blocks matched with the double-threaded rod preform opposite linear motions at the same speed so as to drive the direction-controlling continuum structural bones or proximal continuum structural bones connected with the sliding blocks to be pushed or pulled, so that the first or second dual continuum mechanism or third continuum segment can be bent in any direction.

DETAILED DESCRIPTION

In order to make objectives, technical solutions, and advantages of the present disclosure clear, embodiments of the present disclosure will be described in detail with reference to accompanying drawings. It is appreciated that embodiments shown in accompanying drawings are not limitations to the scope of the present disclosure but intended to explain the spirit of embodiments of the present disclosure.

Embodiment 1

Figure 1:
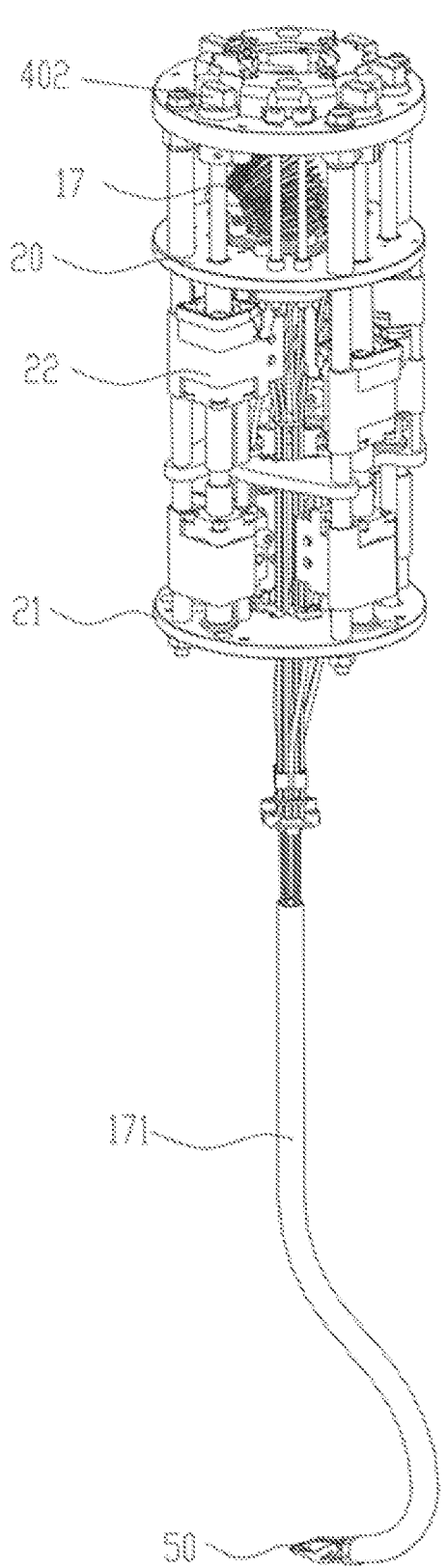
FIG. 1 is a schematic diagram of an overall structure of an embodiment 1 of the present disclosure.
Figure 2:
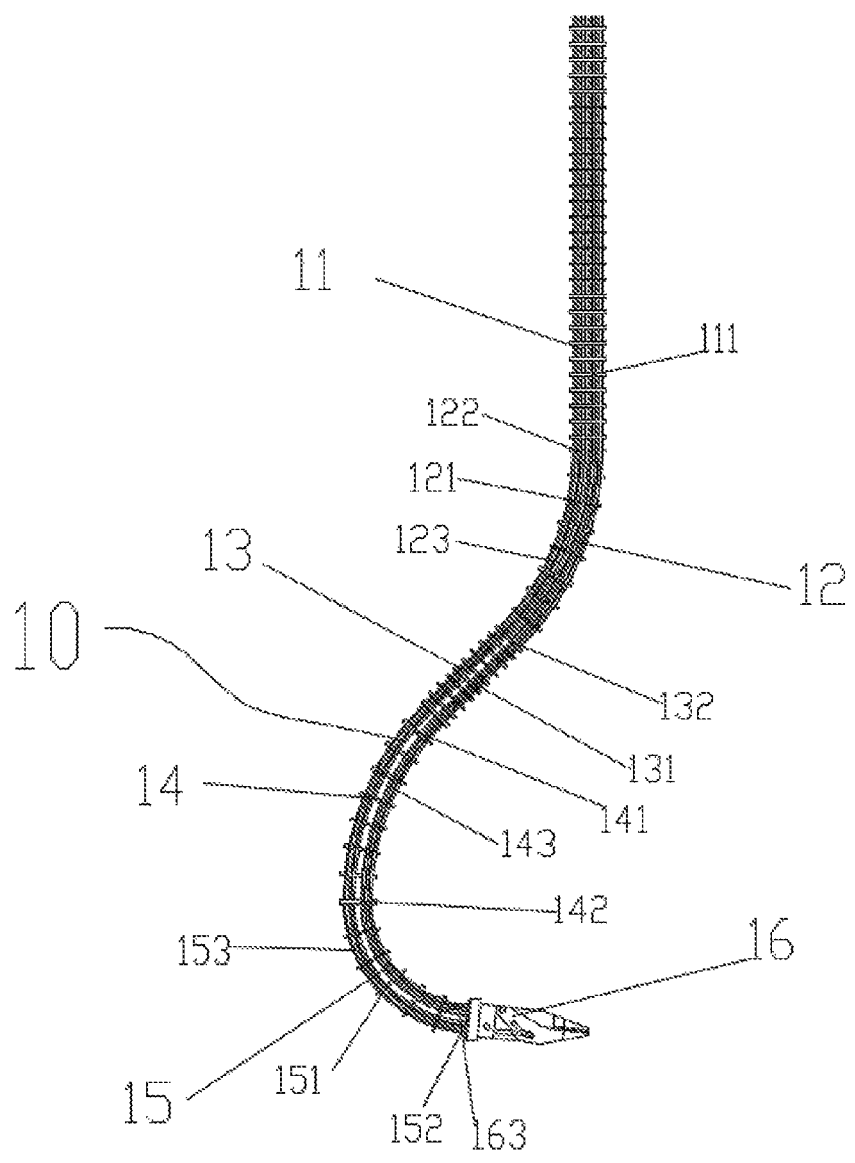
FIG. 2 is a schematic diagram of a structure of a mechanical arm according to the embodiment 1 of the present disclosure.

As shown in FIGS. 1 and 2, a double-bending flexible surgical tool system provided by the embodiment of the disclosure includes a mechanical arm 10, a proximal continuum segment 17 and a transmission driving unit 20. The mechanical arm 10 includes a first continuum segment 12, a rigid connection segment 13, a second continuum segment 14, and a third continuum segment 15. The first continuum segment 12, the rigid connection segment 13, and the second continuum segment 14 are sequentially associated to form a first dual continuum mechanism. The third continuum segment 15 is disposed at a distal end of the second continuum segment 14 and associated with the proximal continuum segment 17 disposed in the transmission driving unit 20 to form a second dual continuum mechanism. The transmission driving unit 20 is associated with the rigid connection segment 13 and the proximal continuum segment 17, respectively, to drive the first continuum segment 12 to bend towards any direction to further drive the second continuum segment 14 to bend towards the opposite direction in a coupling way, and to drive the proximal continuum segment 17 to bend towards any direction to further drive the third continuum segment 15 to bend towards the opposite direction in a coupling way.

Figure 3:
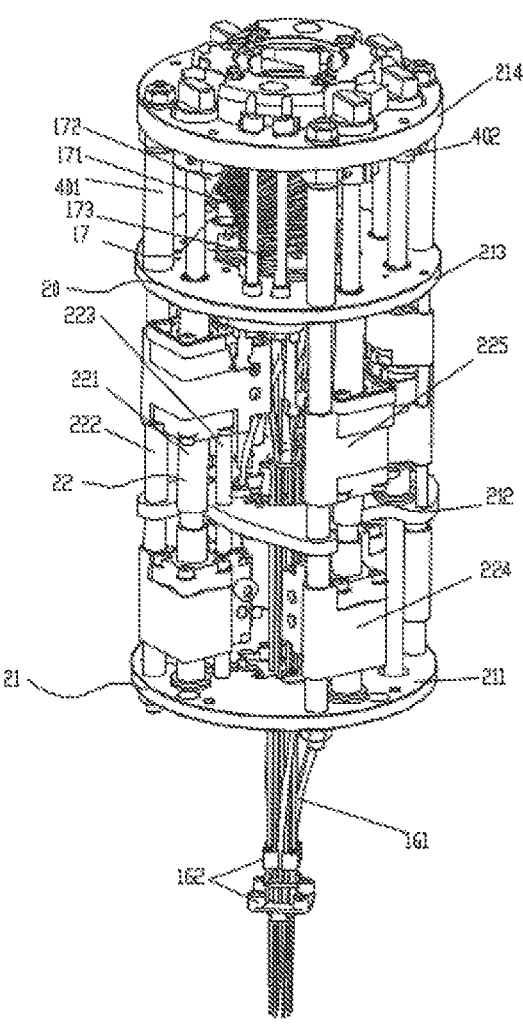
FIG. 3 is a schematic diagram of a transmission driving unit according to the embodiment 1 of the present disclosure.

In this embodiment, as shown in FIG. 3, the transmission driving unit 20 includes a plurality of linear motion mechanisms 22 operable to convert a rotational motion input to a linear motion output. The linear motion mechanism 22 includes: a double-threaded rod 221 that is rotatable and has two threaded sections thereon with threads in opposite directions; a first sliding block 224 and a second sliding block 225 respectively rotatably connected with two threaded sections of the double-threaded rod 221. When the double-threaded rod 221 rotates, the first sliding block 224 and the second sliding block 225 perform opposite linear motions along the double-threaded rod 221 at the same speed.

In the present embodiment, as shown in FIG. 2, the first continuum segment 12 includes a first continuum fixing disk 122 and direction-controlling continuum structural bones 123. The rigid connection segment 13 includes a rigid connection fixing disk 132, and the second continuum segment 14 includes a second continuum fixing disk 142 and first dual continuum structural bones 143. Direction-controlling continuum structural bones 123 include a plurality of pairs. Distal ends of each pair of direction-controlling continuum structural bones 123 are connected with a rigid connection fixing disk 132, and proximal ends of each pair of direction-controlling continuum structural bones 123 pass through the first continuum fixing disk 122 and then are respectively connected with the first sliding block 224 and the second sliding block 225. There are a plurality of first dual continuum structural bones 143. A distal end of each of the first dual continuum structural bones 143 is connected with a second continuum fixing disk 142, and a proximal end is connected with the first continuum fixing disk 122 after passing through the rigid connection fixing disk 132. Thus, first sliding block 224 and second sliding block 225 which are in opposite linear motions can push and pull a pair of direction-controlling continuum structural bones 123 connected thereto, driving the first continuum segment 12 to bend in a certain direction, further driving the second continuum segment 14 to bend in opposite direction in a proportional relationship. Because a length of the first dual continuum structural bone 143 remains unchanged during driving, a total length of the dual continuum mechanism including the first continuum segment 12, the rigid connection segment 13 and the second continuum segment 14 maintains unchanged. Thus, the coupling movement of the second continuum segment 14 is also uniquely determined.

The proximal continuum segment 17 includes a proximal continuum fixing disk 172 and proximal continuum structural bones 173. The third continuum segment 15 includes a third continuum fixing disk 152 and a second dual continuum structural bones 153. Proximal continuum structural bones 173 includes at least two pairs. Distal ends of each pair of proximal continuum structural bones 173 are connected with the proximal continuum fixing disk 172, and proximal ends are directly connected with the first sliding block 224 and the second sliding block 225. There are a plurality of second dual continuum structural bones 153. A distal end of each second dual continuum structural bone 153 is connected with a third continuum distal fixing disk 152, and a proximal end passes through the first continuum fixing disk 122, the rigidly connection fixing disk 132, and the second continuum fixing disk 142 and then is connected with the proximal continuum fixing disk 172. Thus, the first sliding block 224 and the second sliding block 225 which move in opposite linear directions can push and pull a pair of proximal continuum structural bones 173 connected thereto, driving the proximal continuum segment 17 to bend in a certain direction, further driving the third continuum segment 15 to bend in opposite directions in a proportional relationship. Because a length of the second dual continuum structural bone 153 remains unchanged during driving, a total length of the dual continuum mechanism including the third continuum segment 15 and the proximal continuum segment 17 also maintains unchanged. Thus, the coupling movement of the third continuum segment 15 is also uniquely determined.

In addition, the proportional relationship of the bending of the second continuum segment 14 is based on distribution radii of the first dual continuum structural bones 143 in the first continuum segment 12 and the second continuum segment 14. The proportional relationship of the bending of the third continuum segment 15 is based on distribution radii of the second dual continuum structural bones 153 in the third continuum segment 15 and the proximal continuum segment 17. In an embodiment, the distribution radii of the first continuum segment 12 and the second continuum segment 14 are equal, so that the first continuum segment 12 and the second continuum segment 14 bend in an equivalently opposite manner, thereby ensuring that the first continuum fixing disk 122 and the second continuum fixing disk 142 are always parallel to each other during driving.

In the present embodiment, as shown in FIG. 2, the flexible surgical tool system further includes a surgical effector mechanism 16. Surgical effector mechanism 16 includes a surgical effector 50 disposed on third continuum fixing plate 152 and a surgical effector control wire 163. A distal end of the surgical effector control wire 163 is connected with the surgical effector 50, and a proximal end of the surgical effector control wire 163 passes through the mechanical arm 10 and then is connected with the first sliding block 224 or the second sliding block 225, so that opening and closing actions of the surgical effector 50 can be controlled under the driving of the linear motion mechanism 22.

In the present embodiment, the mechanical arm 10 further includes a rigid feed segment 11. The rigid feed segment 11 includes a rigid feed segment spacer disk 111. A plurality of rigid feed segment spacer disks 111 are spaced at the proximal side of the first continuum fixing disk 122. The first continuum segment 12 further includes a first continuum spacer disk 121. A plurality of first continuum spacer disks 121 are spaced between the distal side of the first continuum fixing disk 122 and the proximal side of the rigid connection fixing disk 132. The direction-controlling continuum structural bone 123 sequentially passes through the rigid feed segment spacer disks 111 and the first continuum spacer disks 121 to prevent instability of the direction-controlling continuum structural bone 123 when pushed.

The rigid connection segment 13 further includes rigid connection spacer disk 131. A plurality of rigid connection spacer disks 131 are spaced at distal side of the rigid connection fixing disk 132. The second continuum segment 14 further includes second continuum spacer disk 141. A plurality of second continuum spacer disks 141 are spaced at proximal side of the second continuum fixing disk 142. The first dual continuum structural bone 143 sequentially passes through the first continuum spacer disks 121, the rigid connection spacer disks 131, and the second continuum spacer disks 141 to limit the first dual continuum structural bones 14.

The third continuum segment 15 further includes a third continuum spacer disk 151. A plurality of third continuum spacer disks 151 are spaced between distal side of the third continuum fixing disk 152 and distal side of the second continuum connection fixing disk 142. Both the second dual continuum structural bone 153 and the surgical effector control wire 163 sequentially pass through each rigid feed segment spacer disk 111, the first continuum spacer disk 121, the rigid connection spacer disk 131, the second continuum spacer disk 141, and the third continuum spacer disk 151 to limit the second dual continuum structural bones 153 and prevent instability of the surgical effector control wire 163 when pushed.

Figure 7:
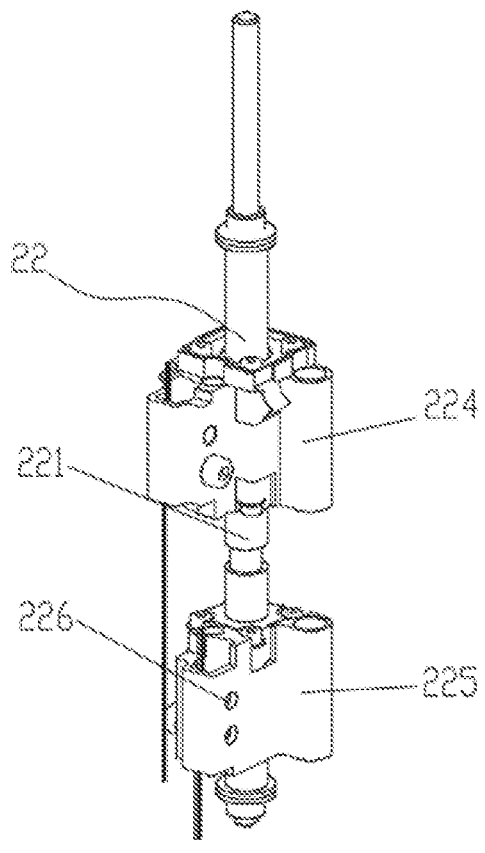
FIG. 7 is a perspective view of a linear motion mechanism of the present disclosure.
Figure 8:
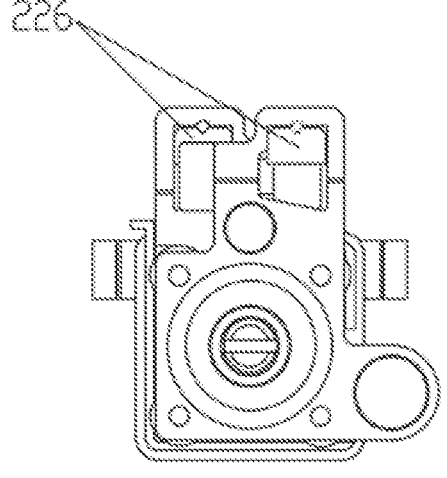
FIG. 8 is a bottom view of the linear motion mechanism of the present disclosure.

In the present embodiment, as shown in FIGS. 3, 7, and 8, the transmission driving unit 20 further includes a base frame 21. The base frame 21 includes a first support plate 211 and a second support plate 213 spaced apart from each other. The double-threaded rod 221 is axially rotatably connected with the first support plate 211 and the second support plate 213. A first guide rod 222 and a second guide rod 223 are axially connected between the first support plate 211 and the second support plate 213. The first sliding block 224 and the second sliding block 225 are slidably connected with the first guide rod 222 and the second guide rod 223, respectively. The first guide rod 222 and the second guide rod 223 have limiting and guiding functions to enable the first sliding block 224 and the second sliding block 225 to smoothly perform opposite linear motions. The base frame 21 includes a compression block 226. The direction-controlling continuum structural bones 123, the proximal continuum structural bones 173, and the surgical effector control wire 163 are secured, by the compression block 226, with the first sliding block 224 and the second sliding block 225.

In this embodiment, the base frame 21 further includes a connection plate 212 disposed between the first support plate 211 and the second support plate 213 and connected with the second guide rod 223. The double-threaded rod 221 passes through the connection plate 212 and has a gap therebetween. The connection plate 212 can separate the two threaded sections of the double-threaded rod 221. the base frame 21 further includes a third support plate 214 connected with the second support plate 213 via a first guide rod 222, so that an arrangement space for other required electrical components is formed between the second support plate 213 and the third support plate 214.

In this embodiment, a positioning sleeve 401 can be disposed over the first guide rod 222 and the second guide rod 223 to position the connection plate 212 and the third support plate 214. Alternatively, the first support plate 211 and the second support plate 213 may be fixedly connected by a threaded support rod, and positioning nuts cooperatively connected with the support rod can position the first support plate 211, the second support plate 213 and the connection plate 212. Therefore, the positioning sleeve 401 can be replaced with the positioning nuts.

In this embodiment, there are five linear motion mechanisms 22. The first pair of linear motion mechanisms 22 can be each connected with a pair of direction-controlling continuum structural bones 123 to achieve the bending degrees of freedom in two directions for first continuum segment 12. A second pair of linear motion mechanisms 22 can be each connected with a pair of proximal continuum structural bones 173 to achieve the bending degrees of freedom in two directions for the third continuum segment 15. And a linear motion mechanism 22 is connected with the surgical effector control wire 163 to control the operation of the surgical effector 50.

In this embodiment, direction-controlling continuum structural bones 123 and second dual continuum structural bones 153 pass through guide plate 162 via guide channels 161 and are connected with first sliding block 224 and second sliding block 225, respectively. Surgical effector control wire 163 passes through guide plate 162 via guide channel 161 and is also connected with first sliding block 224 or second sliding block 225.

In this embodiment, the double-threaded rod 221 is connected with a coupling male connector 402 mounted on the third support plate 214, and then, with the driving motor shaft via the coupling female connector.

Figure 9:
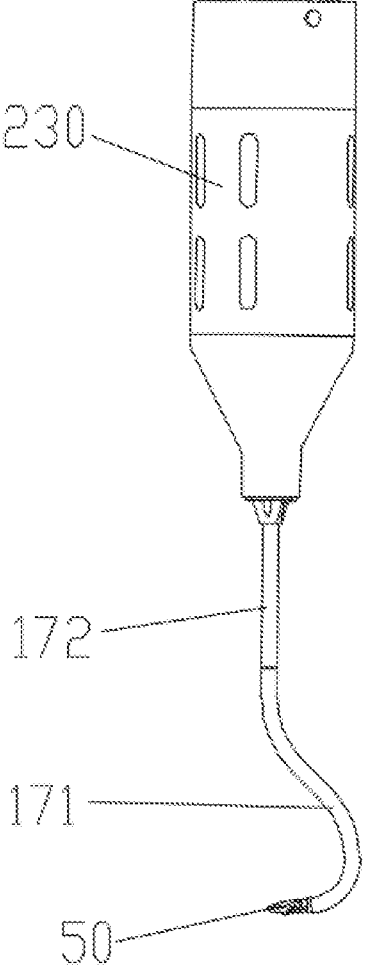
FIG. 9 is a schematic diagram of a structure of an embodiment of the present disclosure after mounting a housing, an envelope and outer sleeve.

In this embodiment, as shown in FIG. 9, a housing 230 is provided outside the transmission driving unit 20. The first support plate 211 and the second support plate 213 are both connected with the housing 230, and an envelope 171 is provided outside the mechanical arm 10 to improve the smoothness of the mechanical arm 10 entering a natural orifice or a surgical incision of a human body. In addition, an outer sleeve 172 can also be provided outside the envelope 171.

Embodiment 2

Figure 4:
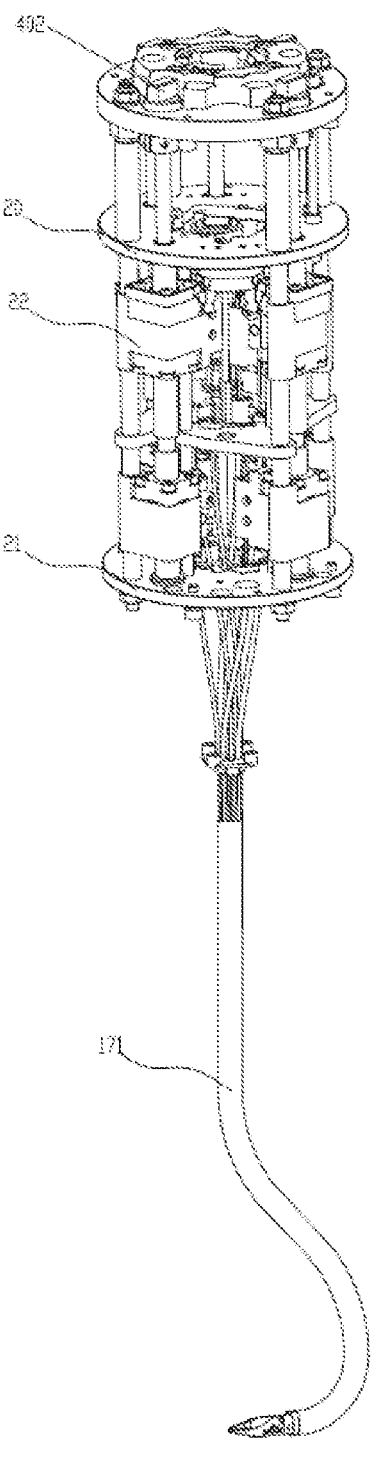
FIG. 4 is a schematic diagram of an overall structure of an embodiment 2 of the present disclosure.
Figure 5:
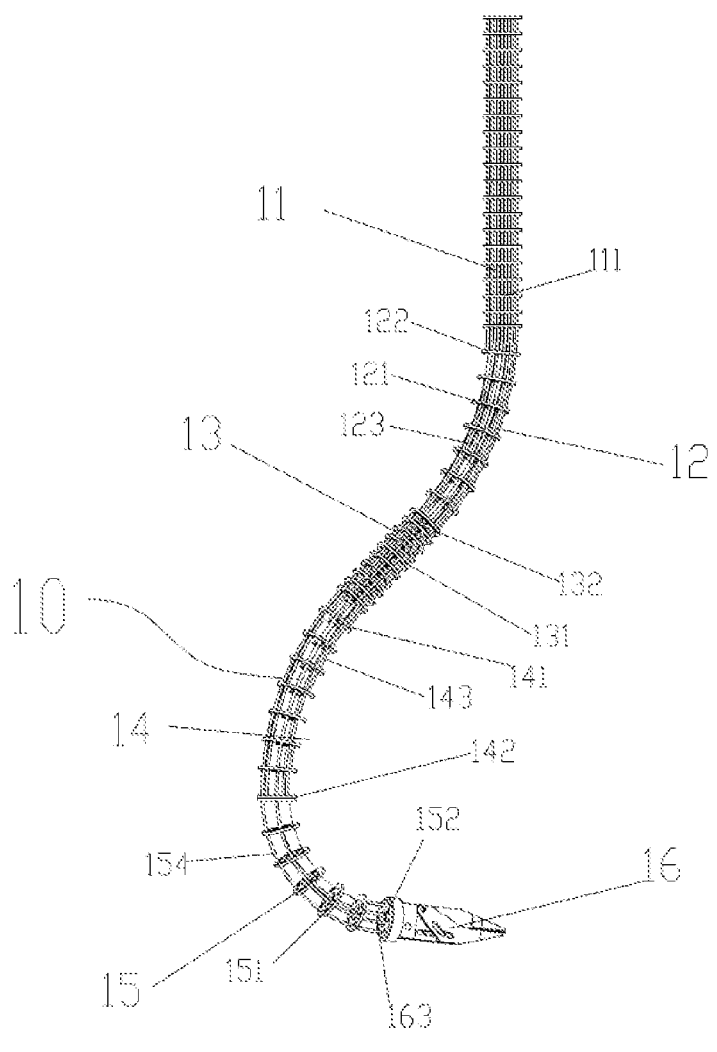
FIG. 5 is a schematic diagram of a structure of a mechanical arm of the embodiment 2 of the present disclosure.

As shown in FIGS. 4 and 5, the embodiment of the disclosure provides a double-bending flexible surgical tool system, including a mechanical arm 10 and a transmission driving unit 20. The mechanical arm 10 includes a first continuum segment 12, a rigid connection segment 13, a second continuum segment 14 and a third continuum segment 15. The first continuum segment 12, the rigid connection segment 13 and the second continuum segment 14 are sequentially associated to form a first dual continuum mechanism. A third continuum segment 15 is disposed at distal end of the second continuum segment 14. The transmission driving unit 2 is respectively connected with the rigid connection segment 13 and the third continuum segment 15 to drive the first continuum segment 12 to bend towards any direction to further drive the second continuum segment 14 to bend towards the opposite direction, and to directly drive the third continuum segment 15 to bend towards any direction.

Figure 6:
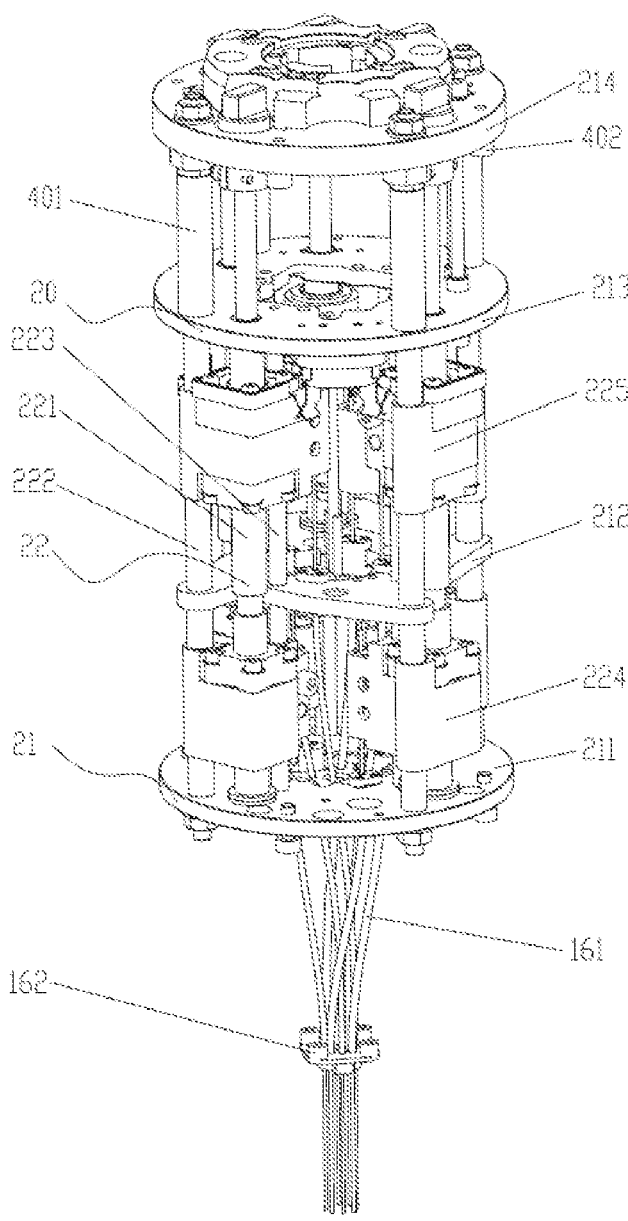
FIG. 6 is a schematic diagram of a transmission driving unit according to the embodiment 2 of the present disclosure.

In the present embodiment, as shown in FIG. 6, the transmission driving unit 20 includes a plurality of linear motion mechanisms 22 operable to convert a rotational motion input to a linear motion output. The linear motion mechanisms 22 including: a double-threaded rod 221 rotatable and having two threaded sections thereon with threads in opposite directions, a first sliding block 224 and a second sliding block 225 rotatably connected with two threaded sections of the double-threaded rod 221, respectively. When the double-threaded rod 221 rotates, the first sliding block 224 and the second sliding block 225 perform opposite linear motions along the double-threaded rod 221 at the same speed.

In the present embodiment, as shown in FIG. 5, the first continuum segment 12 includes a first continuum fixing disk 122 and direction-controlling continuum structural bones 123. The rigid connection segment 13 includes a rigid connection fixing disk 132. The second continuum segment 14 includes a second continuum fixing disk 142 and first dual continuum structural bones 143. Direction-controlling continuum structural bones 123 include a plurality of pairs. Distal ends of each pair of direction-controlling continuum structural bones 123 are connected with a rigid connection fixing disk 132, and proximal ends of each pair of direction-controlling continuum structural bones 123 pass through first continuum fixing disk 122 and then is respectively connected with first sliding block 224 and second sliding block 225. There are a plurality of first dual continuum structural bones 143. Distal end of each of the first due continuum structural bones 143 is connected with a second continuum fixing disk 142, and the proximal end is connected with the first continuum fixing disk 122 after passing through the rigid connection fixing disk 132. The first sliding block 224 and the second sliding block 225 which perform opposite linear motions can push and pull a pair of direction-controlling continuum structural bones 123 connected therewith to drive the first continuum structural section 12 to bend towards a direction so as to drive the second continuum structural section 14 to bend towards the opposite direction in a certain proportional relationship. Because a length of the first dual continuum structural bone 143 remains unchanged during driving, a total length of the dual continuum mechanism including the first continuum segment 12, the rigid connection segment 13, and the second continuum segment 14 remains unchanged, and the coupling movement of the second continuum segment 14 is also uniquely determined.

The third continuum segment 15 includes a third continuum fixing disk 152 and third continuum structural bones 154. The third continuum structural bones 154 includes at least two pairs. Distal ends of each pair of third continuum structural bones 154 are connected with a third continuum distal fixing disk 152, and proximal ends are connected with the first sliding block 224 and the second sliding block 225 after passing through the first continuum fixing plate 122, the rigid connection fixing disk 132, and the second continuum fixing disk 142. The first sliding block 224 and the second sliding block 225 which move in opposite linear directions can push and pull a pair of third continuum structural bones 154 connected therewith to directly drive the third continuum structural section 15 to bend in a certain direction. Since a length of the third continuum structural bone 154 remains unchanged during driving, the movement of the third continuum structural section 15 is uniquely determined.

In the present embodiment, the flexible surgical tool system further includes a surgical effector mechanism 16. The surgical effector mechanism 16 includes a surgical effector 50 disposed on the third continuum fixing disk 152 and a surgical effector control wire 163. Distal end of the surgical effector control wire 163 is connected with the surgical effector 50, and proximal end of the surgical effector control wire 163 passes through the mechanical arm 10 and then is connected with the first sliding block 224 or the second sliding block 225, so that the opening and closing actions of the surgical effector 50 can be controlled under the driving of the linear motion mechanism 22.

In the present embodiment, the mechanical arm 10 further includes a rigid feed segment 11. The rigid feed segment 11 includes rigid feed segment spacer disks 111 spaced on proximal side of the first continuum fixing disk 122. The first continuum segment 12 further includes a first continuum spacer disk 121. A plurality of first continuum spacer disks 121 are spaced between the distal side of the first continuum fixing disk 122 and the proximal side of the rigid connection fixing disk 132. The direction-controlling continuum structural bone 123 sequentially passes through the rigid feed segment spacer disks 111 and the first continuum spacer disks 121 to prevent instability of the direction-controlling continuum structural bone 123 when pushed.

The rigid connection segment 13 further includes a rigid connection spacer disk 131. A plurality of rigid connection spacer disks 131 are spaced at distal side of the rigid connection fixing disk 132. The second continuum segment 14 further includes a second continuum spacer disk 141. A plurality of second continuum spacer disks 141 are spaced at proximal side of the second continuum fixing disk 142. The first dual continuum structural bone 143 sequentially passes through the first continuum spacer disks 121, the rigid connection spacer disks 131, and the second continuum spacer disks 141 to limit the first dual continuum structural bones 143

The third continuum segment 15 further includes a third continuum spacer disk 151. A plurality of third continuum spacer disks 151 are spaced between distal side of the third continuum fixing disk 152 and distal side of the second continuum fixing disk 142. Both the third continuum structural bone 154 and the surgical effector control wire 163 sequentially pass through the rigid feed segment spacer disks 111, the first continuum spacer disks 121, the rigid connection spacer disks 131, the second continuum spacer disks 141, and the third continuum spacer disks 151 to limit the third continuum structural bones 154 while preventing instability of the surgical effector control wire 163 when pushed.

In the present embodiment, as shown in FIGS. 6-8, the transmission driving unit 20 further includes a base frame 21. The base frame 21 includes a first support plate 211 and a second support plate 213 spaced apart from each other. The double-threaded rod 221 is axially rotatably connected with the first support plate 211 and the second support plate 213. The base frame 21 includes a first guide rod 222 and a second guide rod 223 axially connected between the first support plate 211 and the second support plate 213. The first sliding block 224 and the second sliding block 225 are slidably connected with the first guide rod 222 and the second guide rod 223 respectively. The first guide rod 222 and the second guide rod 223 have limiting and guiding functions to enable the first sliding block 224 and the second sliding block 225 to smoothly perform opposite linear motions. The base frame 21 includes a compression block 226. The direction-controlling continuum structural bones 123, the third continuum structural bones 154, and the surgical effector control wire 163 are secured, by the compression block 226, with the first sliding block 224 and the second sliding block 225.

In this embodiment, the base frame 21 further includes a connection plate 212 disposed between the first support plate 211 and the second support plate 213 and connected with the second guide rod 223. The double-threaded rod 221 passes through the connection plate 212 and has a gap therebetween. The connection plate 212 can separate the two threaded sections of the double-threaded rod 221. The base frame 21 further includes a third support plate 214 connected with the second support plate 213 via a first guide rod 222 so that an arrangement space for other required electrical components is formed between the second support plate 213 and the third support plate 214.

In this embodiment, a positioning sleeve 401 is provided over the first guide rod 222 and the second guide rod 223 to position the connection plate 212 and the third support plate 214. Alternatively, the first support plate 211 and the second support plate 213 may be fixedly connected by a threaded support rod. A positioning nut cooperatively connected with the support rod can position the first support plate 211, the second support plate 213 and the connection plate 212. Thus, the positioning nut can replace the positioning sleeve 401.

In this embodiment, there are five linear motion mechanisms 22. A first pair of linear motion mechanisms 22 can be each connected with a pair of direction-controlling continuum structural bones 123 to achieve the bending degrees of freedom in two directions for the first continuum segment 12. A second pair of linear motion mechanisms 22 can be each connected with a pair of third continuum structural bones 154 to achieve the bending degrees of freedom in two directions for the third continuum segment 15. A linear motion mechanism 22 is connected with the surgical effector control wire 163 to control the operation of the surgical effector 50.

In this embodiment, the direction-controlling continuum structural bone 123 and the third continuum structural bone 154 are connected with the first sliding block 224 and the second sliding block 225, respectively, after passing through guide plate 162 via guide channels 161. The surgical effector control wire 163 is also connected with the first sliding block 224 or the second sliding block 225 after passing through the guide plate 162 via the guide channel 161.

In this embodiment, the double-threaded rod 221 is connected with a coupling male connector 402 mounted on the third support plate 214, and thus, to a driving motor shaft via a coupling female connector.

In this embodiment, as shown in FIG. 9, a housing 230 is provided outside the transmission driving unit 20. The first support plate 211 and the second support plate 213 are both connected with the housing 230. An envelope 171 is provided outside the mechanical arm 10 to improve the smoothness of the mechanical arm 10 entering a natural orifice or a surgical incision of a human body. In addition, an outer sleeve 172 can also be provided outside the envelope 171.

The disclosure is only described with reference to the embodiments above. The structure, the arrangement position and the connection of each component can be changed. On the basis of the technical solutions of the disclosure, improvement and equivalent transformation of individual components according to the principle of the disclosure are not excluded from the protection scope of the disclosure.

The invention claimed is:

1. A double-bending flexible surgical tool system comprising:
    a mechanical arm comprising a first continuum segment, a rigid connection segment, a second continuum segment, and a third continuum segment, the first continuum segment and the second continuum segment being associated to form a first dual continuum mechanism, wherein the first continuum segment comprises a first continuum fixing disk and a plurality of pairs of direction-controlling continuum structural bones, the rigid connection segment comprises a rigid connection fixing disk, and distal ends of the plurality of pairs of direction-controlling continuum structural bones are connected with the rigid connection fixing disk;
    a proximal continuum segment disposed at a proximal end of the first continuum segment and associated with the third continuum segment disposed at a distal end of the second continuum segment to form a second dual continuum mechanism; and
    a transmission driving unit associated with the rigid connection segment and the proximal continuum segment, respectively, and configured to drive the first continuum segment to bend in any direction to drive the second continuum segment to bend in an opposite direction, and to drive the proximal continuum segment to bend in any direction to drive the third continuum segment to bend in an opposite direction.

2. The double-bending flexible surgical tool system of claim 1, wherein:

the transmission driving unit comprises a plurality of linear motion mechanisms comprising a double-threaded rod, a first sliding block, and a second sliding block; and proximal ends of each pair of the direction-controlling continuum structural bones pass through the first continuum fixing disk and are connected with the first sliding block and the second sliding block, respectively.

3. The double-bending flexible surgical tool system of claim 2, wherein:

the proximal continuum segment comprises a proximal continuum fixing disk and at least two pairs of proximal continuum structural bones;

distal ends of each pair of the proximal continuum structural bones are connected with the proximal continuum fixing disk; and proximal ends of each pair of the proximal continuum structural bones are connected with the first sliding block and the second sliding block, respectively.

4. The double-bending flexible surgical tool system of claim 3, wherein:

the third continuum segment comprises a third continuum fixing disk and a plurality of second dual continuum structural bones;

a distal end of each second dual continuum structural bone is connected with the third continuum distal fixing disk; and a proximal end of each second dual continuum structural bone passes through the first continuum fixing disk, the rigid connection fixing disk, and a second continuum fixing disk of the second continuum segment, and is connected with the proximal continuum fixing disk.

5. The double-bending flexible surgical tool system of claim 4, wherein:

the third continuum segment further comprises a plurality of third continuum spacer disks spaced between a proximal side of the third continuum fixing disk and a distal side of the second continuum connection fixing disk; and the plurality of second dual continuum structural bones sequentially pass through first continuum spacer disks, rigid connection spacer disks, second continuum spacer disks, and third continuum spacer disks.

6. The double-bending flexible surgical tool system of claim 4, further comprising a surgical effector mechanism comprising:

a surgical effector disposed on the third continuum fixing disk; and a surgical effector control wire, a distal end of the surgical effector control wire being connected with the surgical effector, and a proximal end of the surgical effector control wire passing through the mechanical arm and being connected with the first sliding block or the second sliding block.

7. The double-bending flexible surgical tool system of claim 3, wherein the plurality of linear motion mechanisms comprises:

a second pair of the linear motion mechanisms each connected with a pair of the proximal continuum structural bones.

8. The double-bending flexible surgical tool system of claim 7, wherein the plurality of linear motion mechanisms comprises:

a third linear motion mechanism connected with a surgical effector control wire to control an action of a surgical effector, a distal end of the surgical effector control wire being connected with the surgical effector disposed on a distal end of the third continuum segment.

9. The double-bending flexible surgical tool system of claim 2, wherein the plurality of linear motion mechanisms comprises:

a first pair of the linear motion mechanisms each connected with a pair of the direction-controlling continuum structural bones.

10. The double-bending flexible surgical tool system of claim 9, wherein the plurality of linear motion mechanisms comprises:

a third linear motion mechanism connected with a surgical effector control wire to control an action of a surgical effector, a distal end of the surgical effector control wire being connected with the surgical effector disposed on a distal end of the third continuum segment.

11. The double-bending flexible surgical tool system of claim 1, wherein:

the mechanical arm further comprises a rigid feed segment comprising a plurality of rigid feed segment spacer disks spaced at a proximal side of the first continuum fixing disk;

the first continuum segment further comprises a plurality of first continuum spacer disks spaced between a distal side of the first continuum fixing disk and a proximal side of the rigid connection fixing disk;

each of the plurality of pairs of direction-controlling continuum structural bones sequentially passes through the plurality of rigid feed segment spacer disks and the plurality of first continuum spacer disks; and the second continuum segment comprises a second continuum fixing disk and a plurality of first dual continuum structural bones, a distal end of each first dual continuum structural bone being connected with the second continuum fixing disk, and a proximal end of each first dual continuum structural bone passing through the rigid connection fixing disk and being connected with the first continuum fixing disk.

12. The double-bending flexible surgical tool system of claim 11, wherein:

the rigid connection segment further comprises a plurality of rigid connection spacer disks spaced at a distal side of the rigid connection fixing disk;

the second continuum segment further comprises a plurality of second continuum spacer disks spaced at a proximal side of the second continuum fixing disk; and each of the plurality of first dual continuum structural bones sequentially passes through the plurality of first continuum spacer disks, the plurality of rigid connection spacer disks, and the plurality of second continuum spacer disks.

13. The double-bending flexible surgical tool system of claim 1, wherein bending of the first continuum segment is in proportion to bending of the second continuum segment.

* * * * *